(12) United States Patent
Mishima et al.

(10) Patent No.: US 7,154,019 B2
(45) Date of Patent: Dec. 26, 2006

(54) INDICATOR ON BODY FLUID ABSORBENT ARTICLE

(75) Inventors: Yoshitaka Mishima, Kagawa-ken (JP); Kaiyo Nakajima, Kagawa-ken (JP); Hisashi Takai, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 295 days.

(21) Appl. No.: 10/743,720

(22) Filed: Dec. 24, 2003

(65) Prior Publication Data

US 2004/0138633 A1   Jul. 15, 2004

(30) Foreign Application Priority Data

Dec. 27, 2002   (JP)   ............... 2002-380202

(51) Int. Cl.
*A61F 13/15*   (2006.01)
(52) U.S. Cl. .................................... 604/361
(58) Field of Classification Search ................. 604/361
See application file for complete search history.

(56) References Cited

U.S. PATENT DOCUMENTS

| | | | |
|---|---|---|---|
| 5,955,187 A * | 9/1999 | McCormack et al. | .... 428/315.5 |
| 6,531,204 B1 * | 3/2003 | Suekane et al. | ............ 428/156 |
| 6,747,185 B1 * | 6/2004 | Inoue et al. | ................. 604/361 |
| 6,949,689 B1 * | 9/2005 | Noda et al. | ................. 604/361 |

FOREIGN PATENT DOCUMENTS

JP   9-299401   11/1997

* cited by examiner

*Primary Examiner*—Tatyana Zalukaeva
*Assistant Examiner*—C. Lynne Anderson
(74) *Attorney, Agent, or Firm*—Lowe Hauptman & Berner LLP

(57) ABSTRACT

An indicator interposed between a liquid-impervious sheet and an absorbent core of a body fluid absorbent article includes a water-absorbent sheet and indication elements held in close contact with the water-absorbent sheet. The water-absorbent sheet is preferably formed from porous thermoplastic films having a total luminous transmittance of 40% or lower in a dry state and 60% or higher in a wet state.

6 Claims, 2 Drawing Sheets

INDICATOR ON BODY FLUID ABSORBENT ARTICLE

BACKGROUND OF THE INVENTION

The present invention relates to indicators used in combination with body fluid absorbent articles such as disposable diapers and making it visually perceivable whether a body fluid absorbent core of the articles is in a wet state or not. The present application is based on, and claims priority from, Japanese Application Serial Number 2002-380202, filed Dec. 27, 2002, the disclosure of which is hereby incorporated by reference in it's entirety.

Various indicators have already been well known, which generally intend to make it visually perceivable from outside a backsheet of a body fluid absorbent article whether urination has occurred or not. For example, an indicator disclosed in Japanese Patent Application Publication No. 1997-299401A is interposed between the backsheet and the body fluid absorbent core. This indicator comprises an ink layer adapted to be observable as this layer is wetted and an ink carrying layer interposed between the ink layer and the backsheet so as to be held in close contact with the ink layer. The ink carrying layer contains a surfactant. The above-cited Publication discloses an embodiment of the indicator in which the ink carrying layer is made of paper materials and, in addition to the first ink layer, a second ink layer is provided.

In the case of the known indicator using a water-absorbent paper as the ink supporting layer on which the ink layer is formed by printing, the water-absorbent paper is required to keep a sufficient dimensional stability and strength during a step of printing as well as during various steps of making diaper. To meet such requirements, the water-absorbent paper used for this application has usually been apt to have a basis weight and a bending stiffness both higher than those of nonwoven fabrics and plastic films used as stock materials for the top- and backsheets, respectively, of the diaper. Such paper interposed between the backsheet and the core inevitably makes a region of the backsheet overlapping the absorbent paper relatively stiff. Sometimes, such relatively stiff backsheet may deteriorate a desired soft touch for the wearer. Furthermore, the water-absorbent paper used for such purpose generally allows the amount of urine absorbed thereby to spread easily in this paper. However, information a mother wishes to acquire is not limited to the information whether urination has occurred or not. The other important information the mother wishes to acquire is how many repeated urinations have occurred and how wide range of the core has been wetted. On the basis of such information, the mother may determine to exchange the used diaper with a fresh diaper. With the indicator made of paper, the wetted range of the core does not often coincide with the wetted range of the indicator and it is difficult to specify the range of the core that is actually wetted on the basis of the wetted range of the indicator. Thus, the known indicator can not sometimes provide the adequate information the mother wishes to acquire.

SUMMARY OF THE INVENTION

It is an object of the present invention to solve the problem accompanying the known indicator using a water-absorbent paper, more specifically, to improve the indicator so that the presence thereof never deteriorates a desired soft touch of the article incorporating such indicator, on one hand, and the indicator can provide a wearer's mother with more plenty information, on the other hand.

According to the present invention, there is provided a body fluid absorbent article comprising a liquid-pervious sheet, a liquid-impervious sheet and a body fluid absorbent core interposed therebetween, an indicator interposed between the liquid-impervious sheet and the core and comprising a water-absorbent sheet which allows the core in a wet state to be visually perceived from outside the liquid-impervious sheet and indication elements temporarily concealed by the water-absorbent sheet.

The article further comprises the water-absorbent sheet which comprises a porous thermoplastic film having an inner surface facing the core and an outer surface facing the liquid-impervious sheet, the film having a total luminous transmittance of 40% or lower in a dry state and 60% or higher in a wet state; and the indication elements being held in close contact with the inner surface.

The present invention may be exploited also in preferred manners as follow:

The thermoplastic film exhibits a Klemm's water-absorbency in a range of 1 to 10 mm.

The thermoplastic film contains 20 to 80 wt % of inorganic particles each having a particle diameter in a range of 0.1 to 10μ.

The thermoplastic film contains 0.5 to 5 wt % of modifier for hydrophilicity.

The inorganic particles are coated with at least a part of the modifier for hydrophilicity.

The thermoplastic film is obtained by extruding thermoplastic containing the inorganic particles to form a starting film and then monoaxially or biaxially stretching this starting film at a ratio of 100 to 300%.

The indication elements comprise layers of print ink or the other coating materials intermittently formed on an inner surface of the water-absorbent sheet.

The indication elements is defined by the core itself.

The thermoplastic film exhibits a water-absorption in a range of 5 to 100 wt %.

In the description of the present invention given hereunder, total luminous transmittances are values determined by the method specified in JIS (Japanese Industrial Standard) K 7105 and Klemm's water-absorbencies are values determined by the method specified in JIS P 8141. Dry state, wet state and water-absorption (wt %) of a thermoplastic film are defined as following: water-absorption is calculated from an equation of $\{(W_0-W_1)/W_0\}\times 100$, where $W_0$ represents a weight of a thermoplastic film in a dry state after let stand for 48 hours at a temperature of 23° C. and a R.H. of 25% and $W_1$ represents a weight of this thermoplastic film in a wet state obtained by immersing this film in distilled water at a temperature of 23° C. for 1 minute and then draining off excessive water from the film held between two filter paper sheets under a surface pressure of 0.14 g/cm$^2$ for 2 seconds. For measurement of water-absorbencies, pieces of the thermoplastic film each having a size of 5×5 cm are used.

DETAILED DESCRIPTION OF THE PREFERRED EMBODIMENTS

Details of an indicator according to the present invention will be more fully understood from the description of a disposable pants-type diaper as one embodiment of a body fluid absorbent article given hereunder with reference to the accompanying drawings.

Figure 1:
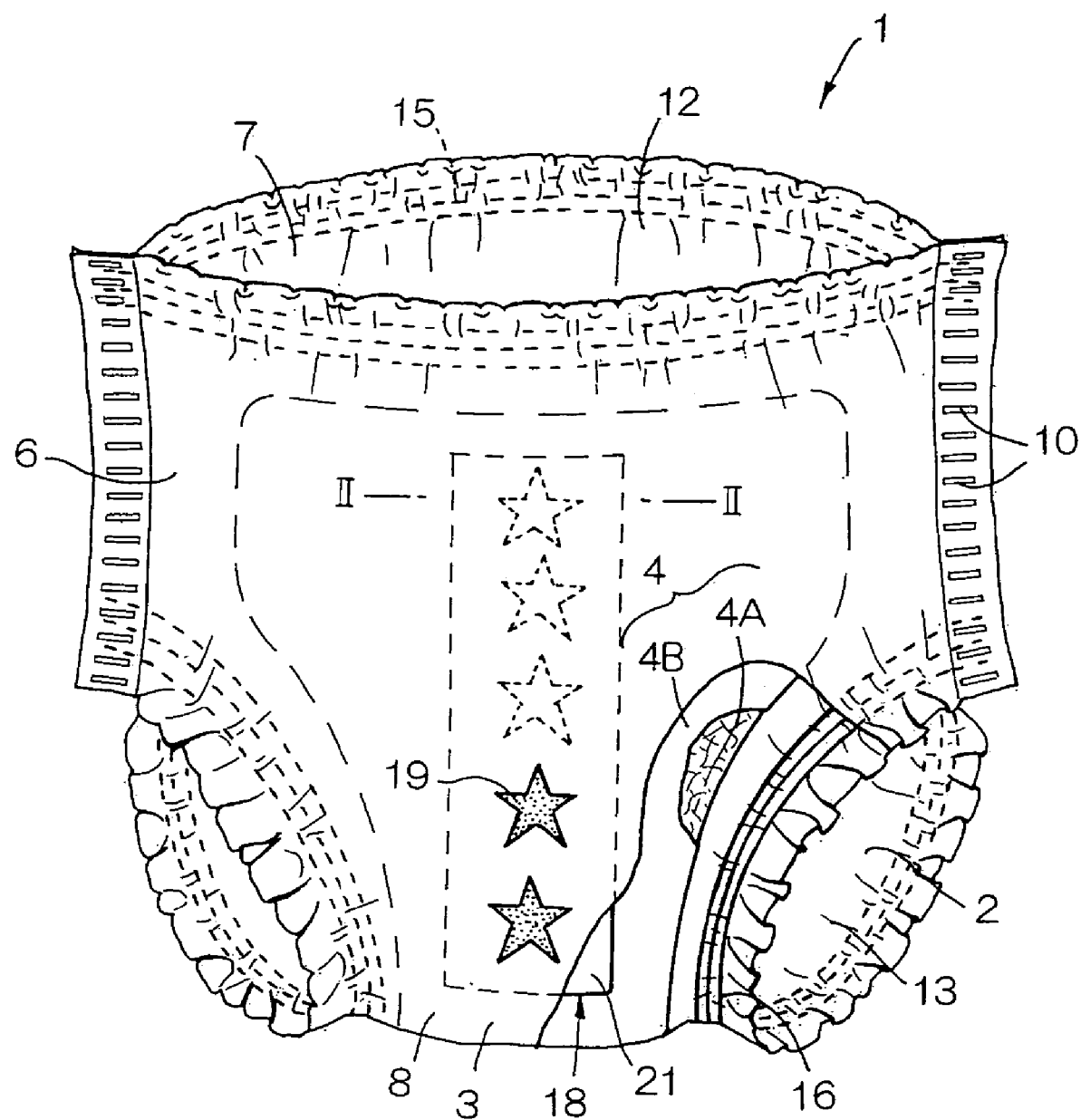
FIG. 1 is a partially cutaway perspective view showing a disposable pants-type diaper.

A disposable pants-type diaper 1 shown by FIG. 1 in a partially cutaway perspective view comprises a liquid-pervious topsheet 2, a liquid-impervious backsheet 3 and an absorbent core 4 interposed between the two sheets 2, 3. Portions of the top- and backsheets 2, 3 extending outward beyond a peripheral edge of the core 4 are overlapped and joined together. The diaper 1 has a front waist region 6, a rear waist region 7 and a crotch region 8 extending between the waist regions 6, 7. Lateral marginal zones of the front and rear waist regions 6, 7 are overlapped and joined together with the topsheet 2 inside at a plurality of spots 10 arranged intermittently in a vertical direction as viewed in FIG. 1. The diaper 1 further has a waist-hole 12 and a pair of leg-holes 13. Along peripheral zones of the waist- and leg-holes 12, 13, a waist elastic member 15 and leg elastic members 16 are attached in a stretched state to the inner surface of at least one of the top- and backsheets 2, 3. In the front waist region 6, an indicator 18 is interposed between the backsheet 3 and the core 4 so that this indicator 18 may inform a wearer's mother of urination occurring.

Stock materials for the topsheet 2 may be selected from a group consisting of a nonwoven fabric and an aperture plastic film. Each of apertures formed through the plastic film preferably has an aperture diameter in a range of 0.5 to 3 mm. Stock materials for the backsheet 3 may be selected from a group consisting of a plastic film and a plastic film laminated on its outer surface with a nonwoven fabric. When the plastic film is in a dry state or the inner surface of the plastic film contacting the core 4 is wetted with urine, the backsheet 3 has a total luminous transmittance in a range of 20 to 80% and allows a display content of the indicator 18, for example, star marks contoured by solid lines in FIG. 1 to be visually perceived from outside the backsheet 3. The core 4 comprises an absorbent material 4A such as fluff pulp or a mixture of fluff pulp and super-absorbent polymer particles and a tissue paper 4B with which the absorbent material 4A is wrapped. The indicator 18 shown in FIG. 1 includes a masking sheet 21 supporting thereon indication elements 19 in the form of five star marks. In the state illustrated by FIG. 1, two of these star marks contoured by solid lines have become visually perceivable from outside the backsheet 3 and remaining three star marks contoured by imaginary lines are not visually perceivable from outside the backsheet 3.

Figure 2:
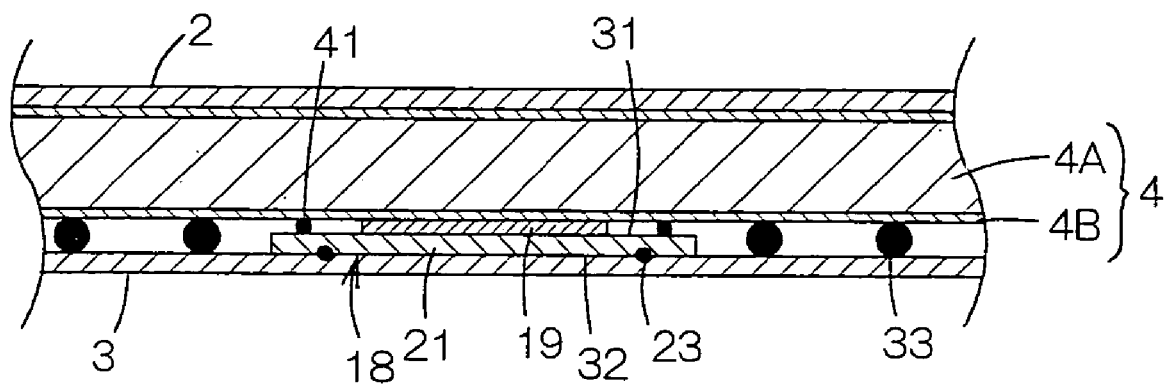
FIG. 2 is a sectional view taken along the line II—II in FIG. 1.

FIG. 2 is a sectional view taken along the line II—II in FIG. 1. As seen in FIG. 2, the indicator 18 comprises the masking sheet 21 and the indication elements 19 held in close contact with the masking sheet 21. The masking sheet 21 is relatively long in the vertical direction as viewed in FIG. 1 and has an outer surface 32 facing the backsheet 3 and an inner surface 31 facing the core 4. The indication elements 19 comprise layers of ink or the other coating material forming five star marks (See FIG. 1) arranged in the vertical direction on the inner surface 31 of the masking sheet 21. The masking sheet 21 is joined to the backsheet 3 by means of intermittently provided adhesives 23 and substantially held in close contact with the backsheet 3. The masking sheet 21 is also held together with the indication elements 19 in close contact with the core 4, preferably joined to the tissue paper 4B by means of hot melt adhesives 41. The backsheet 3 and the tissue paper 4B are joined to each other by means of hot melt adhesives 33.

The masking sheet 21 is formed from water-absorbent thermoplastic films having a plurality of fine apertures and this sheet 21 has total luminous transmittance of 40% or lower in its dry state and 60% or higher in its wet state. Term used herein "dry state thermoplastic film", refers to a thermoplastic film after left stand for 48 hours at a temperature of 23° C. and a R.H. of 75%. Term used herein "wet state thermoplastic film" refers to a dry state thermoplastic film having been immersed in distilled water for 1 minute and thereafter drained off with the film held between two filter paper sheets under a surface pressure of 0.14 g/cm$^2$ for 2 seconds. A preferred thermoplastic film has a water-absorption in a range of 5 to 100 wt % on the basis of a weight of a dry state thermoplastic film. A preferred thermoplastic film has a Klemm's water-absorbency in a range of 1 to 10 mm and retains absorbed water substantially without spreading. Such thermoplastic film is based on polyolefin, for example, high density polyethylene, low density polyethylene or linear low density polyethylene, and obtained by extruding a composition including 20 to 80 wt % of inorganic particles having a particle diameter in a range of 0.1 to 10μ such as valium sulfate, calcium carbonate or titanium oxide and 0.5 to 5 wt % of polyethylene glycol or the like modifying the composition to be hydrophilic to form a starting film which is then monoaxially or biaxially stretched at a ratio in a range of 100 to 300% until a basis weight in a range of 15 to 80 g/m$^2$ is achieved. Whole of the modifier to make the composition hydrophilic may be kneaded in the plastic or a part of modifier may be coated on the inorganic particles. In such thermoplastic film, at least one of the inner and outer surfaces 31, 32 becomes a light scattering rough surface due to the presence of plural inorganic particles and between the inner and outer surfaces 31, 32, moisture-permeable fine apertures are formed around these fine apertures. The maximum particle diameter of the fine aperture is in the order of 10μ. Moisture-permeability of the plural fine apertures as measured by the method specified in JIS (Japanese Industrial Standard) Z 0208 reflects the number of these fine apertures and a preferred moisture-permeability of the thermoplastic film is in a range of 1000 to 6000 g/m$^2$ ·24 hrs. The masking sheet 21 comprising such thermoplastic film contains the hydrophilic modifier and the plural fine apertures, so these fine apertures are flooded and retain water as the film is immersed in water. Thus a high water-absorption is immediately achieved. The total luminous transmittance exhibited by the masking sheet 21 easily rises up to 60% or higher as the inner and outer surfaces 31, 32 are wetted and the water-absorption rises. While it is difficult for the observer to see the indication elements 19 through the outer surface 32 so far as the total luminous transmittance of the masking sheet 21 is 40% or lower, it is easy for the observer to see the indication elements 19 through the masking sheet 21 from its outer surface 32 as the total luminous transmittance reaches 60% or higher.

The indication elements 19 preferably have a color tone distinguished from those of the masking sheet 21 and the backsheet 3. Print ink or coating materials used to form the indication elements 19 preferably is of hydrophilic type and preferably contains light scattering inorganic particles such as silica or alumina so that the indication elements scatter light and make it further difficult to see the indication elements through the masking sheet 21 from its outer surface 32 so far as the core is in a dry state and, when the core is wetted, light scattering is sufficiently reduced to facilitate the observer to see the indication elements 19 through the masking sheet 21 from its outer surface 32. Shape of the indication elements 19 is not limited to that as illustrated and optionally selected.

In the diaper 1 having the indicator 18 constructed as has been described above, the masking sheet 21 may be formed, for example, a low density polyethylene film having a basis weight in a range of 15 to 50 g/m² to avoid an anxiety that this masking sheet 21 might deteriorate a soft touch of the backsheet 3 with which the masking sheet 21 closely contacts. This is for the reason that the low density polyethylene film usually used as stock materials for the backsheet 3 has also a basis weight similar to that of the masking sheet 21. Urine absorbed by the core 4 immediately reaches the masking sheet 21. Thereupon, the inner and outer surfaces 31, 32 of the masking sheet 21 is wetted with urine and simultaneously the plurality of fine apertures formed through the masking sheet 21 are flood with urine. As a result, the inner and outer surfaces 31, 32 of the masking sheet 21 as well as the inner surfaces of the respective fine apertures which have been rough become smooth and the total luminous transmittance of the masking sheet 21 correspondingly rises to 60% or higher. Consequently, it is now possible for the observer to see the indication elements 19 through the backsheet 3 and the masking sheet 21. The masking sheet 21 having a water-absorbency in a range of 1 to 10 mm practically does not spread any quantity of urine. This means that only the portion of the masking sheet 21 contacting the portion of the core 4 wetted with urine exhibits a relatively high total luminous transmittance and one or more of the indication elements 19 lying in this portion become visually perceivable. In other words, the indicator 18 according to the invention makes it possible to determine the portion or the area of the core 4 actually wetted with urine based on the visually perceivable one or more indication elements 19. For example, in FIG. 1, two indication elements 19 in the form of star marks lying on the lower part of the diaper 1 is visually perceivable from outside the backsheet 3, suggesting that the core 4 is wetted until the level defined by these visually perceivable star marks and the upper part of the core 4 is still not wetted. If the area of the core 4 wetted is enlarged due to repeated urination, one or more the remaining indication elements 19 which have not been visually perceivable in FIG. 1 become visually perceivable. In view of its intrinsic function, the indicator 18 may extend in a transverse direction or both in the vertical direction and in the transverse direction, instead of extending in the vertical direction of the diaper 1.

In the present invention, the masking sheet 21 is preferably wetted with urine from its inner surface 31 contacting the core 4. Taking account of a possibility that the layers of print ink or the other coating material might prevent the inner surface 31 of the masking sheet 21 from absorb urine, these layers are preferably locally, i.e., intermittently distributed on the inner surface 31 of the masking sheet 21. For example, each of the star marks may be preferably gravure printed on the inner surface 31 in the form of an assembly of plural spaced dots or the respective star marks are spaced one from another and thereby the area of the masking sheet 21 free from the print ink or the other coating material may be positively defined. Theoretically, the indication elements 19 can be defined as the elements adapted to be visually perceivable as the total luminous transmittance of the masking sheet 21 rises up to the determined level and the masking sheet 21 is also defined as the sheet adapted to temporarily conceal the indication elements 19 and to make the indication elements 19 visually perceivable as the masking sheet 21 is wetted and its total luminous transmittance rises to the predetermined level. In view of this, instead of printing the star marks on the masking sheet 21, the masking sheet 21 may be held in close contact with the core 4 so that the masking sheet 21 is wetted to rise its total luminous transmittance as the core is wetted and the zone exhibiting a sufficient total luminous transmittance to make the core 4 visually perceivable and the zone exhibiting an insufficient total luminous transmittance to make the core 4 visually perceivable may appear on the masking sheet 21. In this case, a boundary between these two zones suggests a range of the core 4 wetted with urine. In this embodiment of the masking sheet 21, the core 4 itself serves as the indication element 19. While the present invention has been described with respect to the disposable pants-type diaper, the invention is applicable also to the indicator on body fluid absorbent articles such as open-type diapers, incontinent diapers or body fluid absorbent pads.

The indicator according to the present invention used with the body fluid absorbent article comprises the masking sheet and the indication elements wherein the masking sheet is formed from flexible thermoplastic films, so there is no anxiety that the presence of the indicator might deteriorate a desired soft touch of the body fluid absorbent article. Furthermore, urine absorbed in the masking sheet substantially does not spread, so it is ensured that the range indicated by the indication elements reliably coincides with the range of the core actually wetted with urine.

What is claimed is:

1. In a body fluid absorbent article comprising:
   a liquid-pervious sheet;
   a liquid-impervious sheet;
   a body fluid absorbent core interposed therebetween;
   an indicator interposed between said liquid-impervious sheet and said core and comprising a water-absorbent sheet which allows said core in a wet state to be visually perceived from outside said liquid-impervious sheet and indication elements temporarily concealed by said water-absorbent sheet;
   said water-absorbent sheet comprising a porous thermoplastic film having an inner surface facing said core and an outer surface facing said liquid-impervious sheet;
   said film having a total luminous transmittance of 40% or lower in a dry state and 60% or higher in a wet state; and
   said indication elements being held in close contact with said inner surface;
   wherein said thermoplastic film contains 0.5 to 5 wt % of modifier for hydrophilicity.

2. The indicator according to claim 1, wherein said inorganic particles are coated with at least a part of said modifier for hydrophilicity.

3. In a body fluid absorbent article comprising:
   a liquid-pervious sheet;
   a liquid-impervious sheet;
   a body fluid absorbent core interposed therebetween;
   an indicator interposed between said liquid-impervious sheet and said core and comprising a water-absorbent sheet which allows said core in a wet state to be visually perceived from outside said liquid-impervious sheet and indication elements temporarily concealed by said water-absorbent sheet;
   said water-absorbent sheet comprising a porous thermoplastic film having an inner surface facing said core and an outer surface facing said liquid-impervious sheet;
   said film having a total luminous transmittance of 40 % or lower in a dry state and 60 % or higher in a wet state; and said indication elements being held in close contact with said inner surface;

wherein said thermoplastic film further contains a hydrophilic modifier for retaining bodily fluid in said apertures and thus increasing water-absorption capability of said thermoplastic film.

4. A body fluid absorbent article, comprising:

a liquid-pervious topsheet;

a liquid-impervious backsheet;

a body fluid absorbent core interposed between said liquid-pervious topsheet and said liquid-impervious backsheet; and a water-absorbent, porous, thermoplastic film interposed between said liquid-impervious backsheet and said core;

said thermoplastic film being attached to said backsheet by adhesive;

said thermoplastic film having a total luminous transmittance of 40% or lower in a dry state, thereby concealing a portion of said core in the dry state;

said thermoplastic film having the total luminous transmittance of 60% or higher in a wet state, thereby allowing said portion of said core to be visible from outside said liquid-impervious backsheet in the wet state;

wherein said thermoplastic film has an inner surface facing and bonded to said core by adhesive, and an outer surface facing and bonded to said liquid-impervious backsheet by adhesive, said thermoplastic film further comprising:

inorganic particles present on at least one of the inner and outer surfaces of said thermoplastic film and making said at least one of the inner and outer surfaces a rough, light scattering surface; and apertures extending through said thermoplastic film and adapted to be filled with bodily fluid for smoothening the rough, light scattering surface and thus increasing the total luminous transmittance of said thermoplastic film; and wherein said thermoplastic film further contains a hydrophilic modifier for retaining bodily fluid in said apertures and thus increasing water-absorption capability of said thermoplastic film.

5. An indicator for use in a body fluid absorbent article comprising a liquid-pervious topsheet, a liquid-impervious backsheet, a body fluid absorbent core interposed between the backsheet and topsheet, said indicator being adapted to be interposed between said backsheet and said core and comprising a water-absorbent, porous, thermoplastic film;

said thermoplastic film having a total luminous transmittance of 40% or lower in a dry state for concealing a portion of said core in the dry state;

said thermoplastic film having the total luminous transmittance of 60% or higher in a wet state for allowing said portion of said core to be visible from outside said liquid-impervious backsheet in the wet state;

said thermoplastic film having an inner surface adapted to face said core, and an outer surface adapted to face said liquid-impervious backsheet;

said thermoplastic film further comprising:

inorganic particles present on at least one of the inner and outer surfaces of said thermoplastic film and making said at least one of the inner and outer surfaces a rough, light scattering surface; and apertures extending through said thermoplastic film and adapted to be filled with bodily fluid for smoothening the rough, light scattering surface and thus increasing the total luminous transmittance of said thermoplastic film;

wherein said thermoplastic film further contains a hydrophilic modifier for retaining bodily fluid in said apertures and thus increasing water-absorption capability of said thermoplastic film.

6. The indicator according to claim 5, consisting of said thermoplastic film.

* * * * *